United States Patent
Huang et al.

(10) Patent No.: US 9,442,077 B2
(45) Date of Patent: Sep. 13, 2016

(54) SCRATCH FILTER FOR WAFER INSPECTION

(71) Applicant: KLA-Tencor Corporation, Milpitas, CA (US)

(72) Inventors: Junqing Huang, Fremont, CA (US); Huan Jin, Dublin, CA (US); Grace Hsiu-Ling Chen, Los Gatos, CA (US); Lisheng Gao, Saratoga, CA (US)

(73) Assignee: KLA-Tencor Corp., Milpitas, CA (US)

( * ) Notice: Subject to any disclaimer, the term of this patent is extended or adjusted under 35 U.S.C. 154(b) by 26 days.

(21) Appl. No.: 14/468,237

(22) Filed: Aug. 25, 2014

(65) Prior Publication Data

US 2015/0063677 A1    Mar. 5, 2015

Related U.S. Application Data

(60) Provisional application No. 61/871,059, filed on Aug. 28, 2013.

(51) Int. Cl.
*G06K 9/62* (2006.01)
*G01N 21/95* (2006.01)
*G06T 5/00* (2006.01)

(52) U.S. Cl.
CPC ............ *G01N 21/9501* (2013.01); *G06T 5/002* (2013.01); *G06T 2207/20061* (2013.01); *G06T 2207/30148* (2013.01)

(58) Field of Classification Search
None
See application file for complete search history.

(56) References Cited

U.S. PATENT DOCUMENTS

| | | |
|---|---|---|
| 3,069,654 A | 12/1962 | Hough |
| 5,418,892 A | 5/1995 | Aghajan et al. |
| 5,430,810 A | 7/1995 | Saeki |
| 5,471,066 A | 11/1995 | Hagiwara |
| 6,229,928 B1 | 5/2001 | Matsuzawa |
| 6,268,935 B1 | 7/2001 | Kingetsu |
| 6,292,583 B1 | 9/2001 | Maruo |
| 6,324,299 B1 | 11/2001 | Sarachik et al. |
| 6,330,354 B1 | 12/2001 | Companion et al. |
| 6,408,105 B1 | 6/2002 | Maruo |
| 6,493,645 B1 | 12/2002 | Hladschik |

(Continued)

FOREIGN PATENT DOCUMENTS

JP    2001-331784    11/2001

OTHER PUBLICATIONS

U.S. Appl. No. 14/450,170 by Huang et al. filed Aug. 1, 2014.
(Continued)

*Primary Examiner* — Brian P Werner
(74) *Attorney, Agent, or Firm* — Ann Marie Mewherter (57) ABSTRACT

Methods and systems for filtering scratches from wafer inspection results are provided. One method includes generating a defect candidate map that includes image data for potential defect candidates as a function of position on the wafer and removing noise from the defect candidate map to generate a filtered defect candidate map. The method also includes determining one or more characteristics of the potential defect candidates based on portions of the filtered defect candidate map corresponding to the potential defect candidates. In addition, the method includes determining if each of the potential defect candidates are scratches based on the one or more characteristics determined for each of the potential defect candidates and separating the potential defect candidates determined to be the scratches from other defects in inspection results for the wafer.

38 Claims, 2 Drawing Sheets

(56) References Cited

U.S. PATENT DOCUMENTS

| | | |
|---|---|---|
| 6,544,805 B2 | 4/2003 | Holcman et al. |
| 6,574,366 B1 | 6/2003 | Fan |
| 6,665,449 B1 | 12/2003 | He et al. |
| 6,763,142 B2 * | 7/2004 | Dai ................. G06T 7/0004 382/145 |
| 6,810,139 B2 | 10/2004 | Smilansky et al. |
| 7,057,721 B2 | 6/2006 | Gardner et al. |
| 7,373,277 B1 * | 5/2008 | Wu ................. G06T 7/0006 702/185 |
| 7,592,616 B1 * | 9/2009 | Velidandla ........... C30B 29/36 250/559.29 |
| 7,711,521 B1 | 5/2010 | Wu et al. |
| 8,223,327 B2 | 7/2012 | Chen et al. |
| 2001/0042705 A1 | 11/2001 | Nakagaki et al. |
| 2002/0181756 A1 | 12/2002 | Shibuya et al. |
| 2003/0132405 A1 | 7/2003 | Some |
| 2004/0064269 A1 | 4/2004 | Shibuya et al. |
| 2004/0220754 A1 | 11/2004 | Brasack et al. |

OTHER PUBLICATIONS

International Search Report and Written Opinion for PCT/US2014/052758 mailed Dec. 9, 2014.

* cited by examiner

SCRATCH FILTER FOR WAFER INSPECTION

BACKGROUND OF THE INVENTION

1. Field of the Invention

This invention generally relates to filtering scratches out of defect detection results of wafer inspection.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

Inspection processes generally detect a significant amount of potential defects that are actually nuisance defects on the wafer or noise. Nuisance defects as that term is generally used in the art can be defined as defects that are detected on the wafer that the user does not care about or events that are detected as defects but are not any kind of actual defects. For instance, in some wafer inspections, defects that are located on layers of the wafer under the layer being inspected can be detected, but those defects on underlying layers may not be of interest for the layer being inspected. In one such instance, scratches from a chemical mechanical polishing (CMP) layer can appear as optically real defects in inspections of later layers. However, scratches may not be defects of interest for the layer being inspected. Therefore, scratches on one layer can cause the nuisance rate of inspection of later layers on a wafer to be higher. As such, detecting such nuisance defects and reporting them as actual defects to a user have a number of disadvantages such as obscuring actual defects that a user cares about and/or affect the device fabrication in a meaningful manner in the inspection results, obstructing process control attempts to correct the actual defects that a user cares about, and causing users to change the wafer inspection process in ways to reduce the detection of nuisance defects that cause fewer defects of interest to be detected.

Since nuisance defects will be detected by most every inspection process, many inspection processes have been developed in which defect detection is performed and then the detected defects are filtered in some manner to separate defects of interest from nuisance defects. For instance, when there may be previous layer scratches detected in an inspection process, the inspection process may include using size or shape features to filter out relatively large scratches. Such filtering may be effective for some scratches but perhaps not all scratches. For instance, scratches caused by a CMP process include micro-scratches, which can have a substantially faint tail. Regular inspection processes may not detect the relatively faint tail of the micro-scratches. Therefore, only a portion of a micro-scratch having a relatively faint tail can appear in defect detection results thereby causing the micro-scratch to appear to have a shape in an image of the wafer that is different from its actual shape on the wafer. As such, defect filtering that is performed based on the shape of defects may not classify such micro-scratches as scratch defects. Consequently, the wafer inspection results may include a significant number of micro-scratches. In addition, since 60% to 70% of scratches caused by CMP processes can be micro-scratches having relatively faint tails, the wafer inspection results may include a significant percentage of all of the scratches on the wafer.

Accordingly, it would be advantageous to develop methods and systems for filtering defects detected on wafers that can be used to more effectively reduce the nuisance rate of inspection processes for wafers due to micro-scratches on the wafers.

SUMMARY OF THE INVENTION

The following description of various embodiments is not to be construed in any way as limiting the subject matter of the appended claims.

One embodiment relates to a computer-implemented method for filtering scratches from inspection results for a wafer. The method includes generating a defect candidate map for a wafer from images of the wafer generated by a wafer inspection system. The defect candidate map includes image data for potential defect candidates as a function of position on the wafer. The method also includes removing noise from the defect candidate map to generate a filtered defect candidate map. In addition, the method includes determining one or more characteristics of the potential defect candidates based on portions of the filtered defect candidate map corresponding to the potential defect candidates. The method further includes determining if each of the potential defect candidates are scratches based on the one or more characteristics determined for each of the potential defect candidates. The method also includes separating the potential defect candidates determined to be the scratches from other defects in inspection results for the wafer generated by the wafer inspection system. The generating, removing, determining the one or more characteristics, determining if each of the potential defect candidates are scratches, and separating steps are performed by a computer system.

Each of the steps of the method described above may be performed as described further herein. The method described above may include any other step(s) of any other method(s) described herein. The method described above may be performed using any of the systems described herein.

Another embodiment relates to a non-transitory computer-readable medium storing program instructions executable on a computer system for performing a computer-implemented method for filtering scratches from inspection results for a wafer. The computer-implemented method includes the steps of the computer-implemented method described above, which may be performed as described further herein. In addition, the computer-implemented method for which the program instructions are executable may include any other step(s) of any other method(s) described herein. The non-transitory computer-readable medium may be further configured as described herein.

An additional embodiment relates to a system configured to filter scratches from inspection results for a wafer. The system includes an optical subsystem configured to direct light to a wafer and detect light from the wafer to thereby generate images for the wafer. The system also includes a computer subsystem configured for performing the generating, removing, determining the one or more characteristics, determining if each of the potential defect candidates are the scratches, and separating steps described above. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

Figure 1:
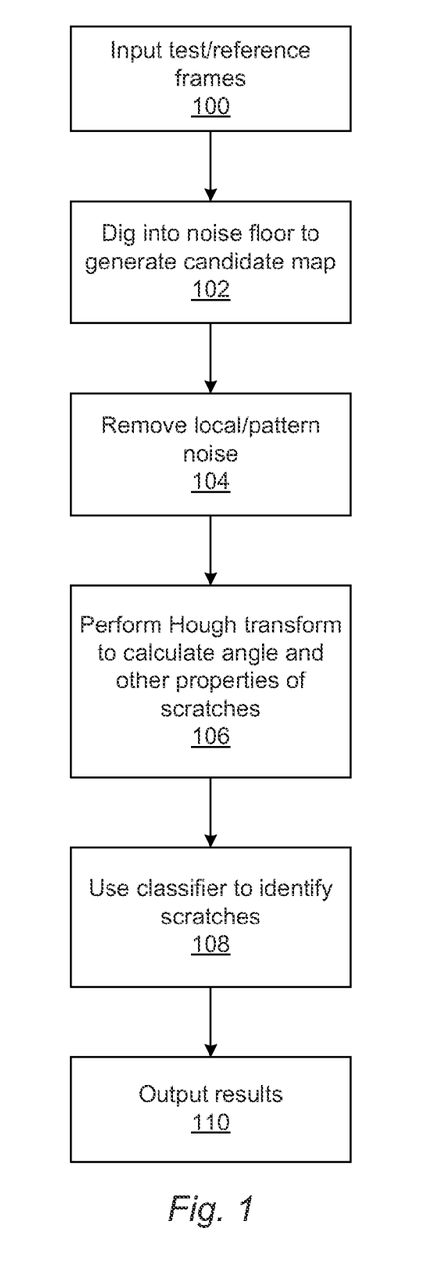
FIG. 1 is a flow chart illustrating one embodiment of a computer-implemented method for filtering scratches from inspection results for a wafer.

One embodiment relates to a computer-implemented method for filtering, scratches from inspection results for a wafer. FIG. 1 illustrates one embodiment of such a computer-implemented method. The computer-implemented method may include acquiring the inspection results using the inspection system. For example, acquiring the inspection results may include scanning light over the wafer, generating output (e.g., images or image data) responsive to light from the wafer detected by the inspection system during the scanning, detecting defects on the wafer based on the output, and generating the inspection results to include information about the defects. In this manner, acquiring the inspection results may include scanning the wafer. However, acquiring the inspection results does not necessarily include scanning the wafer. For example, acquiring the inspection results may include acquiring the inspection results from a storage medium in which the inspection results have been stored (e.g., by the inspection system). Acquiring the inspection results from the storage medium may be performed in any suitable manner, and the storage medium from which the inspection results are acquired may include any of the storage media described herein. Images used in the embodiments described herein may be acquired in similar manners (e.g., by scanning the wafer or from a storage medium in which the images are stored).

The method includes generating a defect candidate map for a wafer from images of the wafer generated by a wafer inspection system. For example, as shown in step 100 of FIG. 1, the input to the method may include input test/ reference ("ref") frames. The test image frames and the reference image frames may include image frames for any two dies on the wafer such as two dies that are adjacent to each other on the wafer. However, any other reference and test image frames known in the art may be used in the embodiments described herein (e.g., image frames for cells, fields, etc.). The defect candidate map includes image data for potential defect candidates as a function of position on the wafer. The potential defect candidates may be detected in the image data generated for the wafer as described further herein. The defect candidate map may have any suitable format. Different detect candidate maps may be generated for different potential defect candidates. For example, each of the defect candidate maps may include a predetermined number of pixels surrounding the location of a detected potential defect candidate.

In one embodiment, images of the wafer described further herein are generated by the wafer inspection system detecting light from the wafer. The wafer inspection system may be configured as described further herein. In some embodiments, the scratches are caused by a chemical mechanical polishing (CMP) process performed on the wafer. In a further embodiment, the scratches are located under a layer of the wafer for which the inspection results were generated. For example, scratches from a CMP layer usually appear as optically real defects in inspection of later layers formed on a wafer. In other words, the scratches on a layer under the one being inspected can appear in the images of the wafer generated during inspection and can be detected as defects even though they are not located on the layer being inspected. In addition, such scratches are not defects of interest (DOI) for the inspection of those later layers. Therefore, the scratches are nuisance defects (i.e., defects the user does not care about) and, as such, the scratches can increase the nuisance rate of wafer inspection tools. One advantage of the embodiments described herein is that they can better class scratches and furthermore can filter out scratches without hurting DOI captures.

In one embodiment, generating the defect candidate map includes applying a threshold to the images and determining that portions of the images having values above the threshold are the potential defect candidates. In one such embodiment, the threshold is substantially close to a noise floor in the images. In this manner, as shown in step 102 of FIG. 1, the method may include "digging" into the noise floor to generate a candidate map. The threshold used to generate a candidate map that will be used as described further herein can be lowered into the noise floor level in an attempt to find the faint tail of micro-scratches. "Micro-scratches" as that term is used herein generally refers to scratches caused by CMP processes that have lengths on the order of microns. "Micro-scratches" are also not usually very deep along the entire length of the scratches. In this manner, a "tail" of the scratches may appear substantially faint in images of the wafer compared to the "head" of the scratches. Micro-scratches can also have multiple parts of the tail which are disconnected from each other but the shape of the outline that connects the multiple parts forms a "scratch line."

The embodiments described herein can dig into the noise floor trying to find the faint tails of micro-scratches using the threshold described above. Using such a threshold to detect the potential defect candidates is advantageous since 60% to 70% of scratches are micro-scratches with faint fails. Regular inspection will not catch the faint tails of micro-scratches and thus will fail to classify them as scratches (e.g., they would be classified as another type of defect). In some embodiments, a regular inspection can be performed on a wafer with a normal value of a threshold and then only the pixels surrounding defects detected in the regular inspection could be examined using the threshold at or near the noise floor. In this manner, the entire area of the wafer scanned by the wafer inspection system can be inspected for defects, and then only the areas around (e.g., next to or near) the detected defects can be inspected with a threshold near the noise floor in an attempt to see if the defects extend beyond their originally detected pixels. In this manner, previously undetected portions of scratches can be detected with the noise floor level threshold. In another such embodiment, the images of the wafer include gray scale images. In this manner, the candidate map may be formed by thresholding gray scale images.

The method also includes removing noise from the defect candidate map to generate a filtered defect candidate map. In one embodiment, the noise that is removed from the defect candidate map includes local color noise. In one such embodiment, removing the noise includes applying a local difference filter to the images. In this manner, the local color noise can be mitigated by removing the noise source of local color using a difference filter. "Local color variation" refers to color variation in images or image data for the wafer due to process variations on the wafer. Local color noise in the images may also be filtered as described in U.S. patent application Ser. No. 14/450,170 by Huang et al. filed Aug. 1, 2014, which is incorporated by reference as if fully set forth herein. In another embodiment, the noise that is removed from the defect candidate map includes pattern noise. In one such embodiment, removing the noise includes removing horizontal and vertical pattern noise from the images. In this manner, the pattern noise can be mitigated by removing horizontal and vertical pattern residues. For example, filtering the pattern noise may include suppressing horizontal pattern noise by removing relatively long lines. In addition, the embodiments described herein can be configured to remove both local color and pattern noise. For example, as shown in FIG. 1, the method may include removing local color/pattern noise in step 104. Therefore, the embodiments described herein can mitigate noise sources of local color variation and pattern noise. The embodiments described herein can also or alternatively be configured to remove any other noise sources in the defect candidate map.

In addition, the method includes determining one or more characteristics of the potential defect candidates based on portions of the filtered defect candidate map corresponding to the potential defect candidates. In one embodiment, determining the one or more characteristics includes applying a simplified Hough transform to the portions of the filtered defect candidate map corresponding to the potential defect candidates to thereby determine the one or more characteristics of the potential defect candidates. The simplified Hough transform may include any suitable form of the Hough transform and can be applied to the portions of the filtered defect candidate map corresponding to the potential defect candidates in any suitable manner. The one or more characteristics may, however, be determined using any other suitable algorithm and/or method known in the art. For instance, the one or more characteristics may be determined by using a geometric method to find the scratch head and tail angles.

In one embodiment, the one or more characteristics include angle of orientation of the potential defect candidates on the wafer. For example, as shown in step 106 of FIG. 1, a simplified version of the Hough transform may be used to calculate the angle and other properties of scratches. In this manner, the embodiments described herein may include calculating any Hough-based features and other features of the defect candidates (e.g., orientation, head magnitude, tail magnitude, size of tail and scratch confidence). In another embodiment, applying the simplified Hough transform includes applying the simplified Hough transform to only the portions of the filtered defect candidate map corresponding to the potential defect candidates. For example, the simplified Hough transform can be used to calculate the Hough transform from only the defective pixels, instead of all pixels.

The embodiments described herein may use a simplified Hough transform and mitigations on local color and pattern noise to increase the ability of micro-scratch classification. For example, the method further includes determining if each of the potential defect candidates are scratches based on the one or more characteristics determined for each of the potential defect candidates. Determining if the potential defect candidates are scratches may be performed using a simple classifier to decide if a detected defect is actually a scratch. A "simple" classifier may be any classifier that can classify scratches using decision rules based on scratch features such as those described further herein. For example, as shown in step 108 of FIG. 1, the method may include using a classifier to identify scratches.

In one embodiment, the scratches include heads that appear stronger in the images than tails of the scratches. In one such embodiment, generating the inspection results for the wafer includes applying a threshold to the images of the wafer generated by the wafer inspection system, and the tails of the scratches have values in the images that are approximately equal to or less than the threshold. In another such embodiment, the one or more characteristics include magnitude of the heads and tails in the images. In an additional such embodiment, the one or more characteristics include angles of orientation of the heads and the tails. In a further such embodiment, the one or more characteristics include number of pixels in the tails. For example, the simple classifier described above may utilize information of (1) the magnitude of both the head and tail of an inspected defect, (2) the angle formed from the head and tail, (3) how many pixels are in the tail, and (4) the confidence of that head and tail form a scratch.

In one example, if the maximum magnitude of the head portion is below a certain predetermined threshold (determined based on the wafer and inspection system characteristics), then the head portion may be determined to not be part of a scratch. In another example, if the magnitude of the tail portion of a potential defect candidate is less than a first predetermined threshold or greater than a second predetermined threshold (i.e., not between two predetermined thresholds, which are wafer and inspection system dependent), then the defect candidate that includes the tail portion may be determined to not be a scratch. In addition, if the number of pixels in a potential defect candidate in the main direction of the defect candidate is less than a certain number (e.g., 3), then the defect candidate may be determined to not be a scratch. Furthermore, if the directions of the head portion and tail portion of a potential defect candidate do not agree with each other (i.e., scratch confidence is low), then the potential defect candidate may be determined to not be a scratch. In addition, if the direction of a potential defect candidate is horizontal or vertical, then the potential defect candidate may be determined to not be a scratch. Moreover, if a primary portion of a potential defect candidate is not strong, then the potential defect candidate may be determined to not be a scratch.

In contrast, if the maximum magnitude of the head portion of a potential defect candidate is above the certain predetermined threshold, if the magnitude of the tail portion is between the first and second predetermined thresholds, if the number of pixels in the main direction of the potential defect candidate is equal to or greater than the certain number, if the major and second directions agree with each other, if the direction of the potential defect candidate is not horizontal or vertical, and if the primary portion of the potential defect candidate is strong, then the potential defect candidate may be determined to be a scratch. Therefore, the classifier described above may be configured to compare the characteristics described above to a number of different benchmarks that separate values of the characteristics that are indicative of scratches and those that are not characteristic of scratches. The characteristics described above may be considered in a different order than that described above. In addition, any other suitable characteristics may be added to those described above if they can be used to separate scratches from non-scratches.

The method also includes separating the potential defect candidates determined to be the scratches from other defects in inspection results for the wafer generated by the wafer inspection system. Separating the potential defect candidates determined to be scratches from other defects may include eliminating the scratches from the inspection results. In this manner, the method may include outputting final results, as shown in step 110 of FIG. 1, that include mostly DOI and almost no scratch and micro-scratch nuisance defects. However, separating the potential defect candidates determined to be scratches from other defects may include separating the scratches into a different classified bin than other current layer defects. In this manner, a user can keep track of both previous layer and current layer defects in one inspection check point.

The embodiments described herein, therefore, can be used as scratch filters and provide a reliable classification solution for micro-scratches for the first time. In contrast, the previously used scratch filters can only classify relatively large scratches and there was no solution for micro-scratch classification. In this manner, the embodiments described herein provide opportunities for enhancement of tool sensitivity (i.e., better sensitivity for wafer inspection tools) by reducing the nuisance rate and providing yield relevant defects to wafer inspection tool users.

The embodiments described herein are different from previously used methods for filtering scratches from inspection results in a number of important ways. For example, the embodiments described herein do not assume the size of the scratch (as many micro-scratches can be substantially small with a relatively faint tail, but bigger scratches can span over many pixels). In contrast, some previously used methods use size as a requirement for spatial characteristics of potential defect candidates and try to search for scratches with the same size on an image. Also, some previously used methods require the scratches to be wholly included in a sub-image of an entire wafer image, while the embodiments described herein do not require that.

Generating the defect candidate map, removing noise from the defect candidate map, determining the one or more characteristics, determining which of the potential defect candidates are scratches, and separating the potential defect candidates determined to be the scratches are performed by a computer system, which may be configured as described further herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Figure 2:
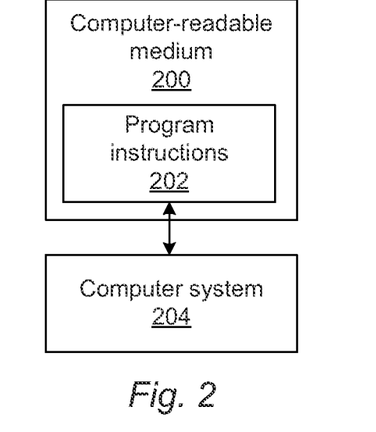
FIG. 2 is a block diagram illustrating one embodiment of a non-transitory computer-readable medium storing program instructions executable on a computer system for performing one or more of the computer-implemented method embodiments described herein.

Another embodiment relates to a non-transitory computer-readable medium storing program instructions executable on a computer system for performing a computer-implemented method for filtering scratches from inspection results for a wafer. One such embodiment is shown in FIG. 2. For example, as shown in FIG. 2, non-transitory computer-readable medium 200 includes program instructions 202 executable on computer system 204 for performing the computer-implemented method for filtering scratches from inspection results for a wafer described above. The computer-implemented method for which the program instructions are executable may include any other step(s) of any other method(s) described herein.

Program instructions 202 implementing methods such as those described herein may be stored on non-transitory computer-readable medium 200. The computer-readable medium may be a storage medium such as a magnetic or optical disk, a magnetic tape or any other suitable computer-readable medium known in the art.

The program instructions may be implemented in any of various ways, including procedure-based techniques, component-based techniques, and/or object-oriented techniques, among others. For example, the program instructions may be implemented using Matlab, Visual Basic, ActiveX controls, C, objects, C#, JavaBeans, Microsoft Foundation Classes ("WC"), or other technologies or methodologies, as desired.

Computer system 204 may take various forms, including a personal computer system, mainframe computer system, workstation, system computer, image computer, programmable image computer, parallel processor, or any other device known in the art. In general, the term "computer system" may be broadly defined to encompass any device having one or more processors, which executes instructions from a memory medium.

Figure 3:
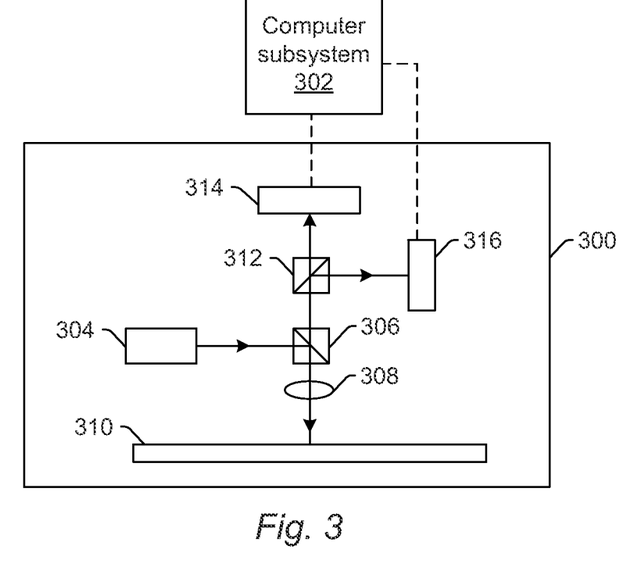
FIG. 3 is a schematic diagram illustrating a side view of one embodiment of a system configured to filter scratches from inspection results for a wafer.

An additional embodiment relates to a system configured to filter scratches from inspection results for a wafer. One embodiment of such a system is shown in FIG. 3. As shown in FIG. 3, the system includes optical subsystem 300 and computer subsystem 302. The optical subsystem is configured to direct light to a wafer and detect light from the wafer to thereby generate images for the wafer. For example, as shown in FIG. 3, the optical subsystem includes light source 304, which may include any suitable light source known in the art.

Light from the light source may be directed to beam splitter 306, which may be configured to direct the light from the light source though lens 308 to wafer 310. The light source may be coupled to any other suitable elements (not shown) such as one or more condensing lenses, collimating lenses, relay lenses, objective lenses, apertures, spectral filters, polarizing components and the like. As shown in FIG. 3, the light may be directed to the wafer at a normal angle of incidence. However, the light may be directed to the wafer at any suitable angle of incidence including near normal and oblique incidence, in addition, the light or multiple light beams may be directed to the wafer at more than one angle of incidence sequentially or simultaneously. The optical subsystem may be configured to scan the light over the wafer in any suitable manner.

Light reflected from wafer 310 may be collected and detected by multiple channels of the optical subsystem during scanning. For example, light specularly reflected from wafer 310 may be collected by lens 308. Lens 308 may include a refractive optical element as shown in FIG. 3. In addition, lens 308 may include one or more refractive optical elements and/or one or more reflective optical elements. Light collected by lens 308 may be directed through beam splitter 306 to beam splitter 312, which may be configured to separate the light into two different paths, one of which is directed to detector 314 and another of which is directed to detector 316. The beam splitters shown in FIG. 3 may include any suitable beam splitters known in the art. The detectors shown in FIG. 3 may include any suitable detectors known in the art such as charge coupled devices (CCDs) or another type of imaging detectors. Detectors 314 and 316 are configured to generate images that are responsive to the specularly reflected light. Therefore, each of the detectors form one channel of the optical subsystem.

Since the optical subsystem shown in FIG. 3 is configured to detect light specularly reflected from the wafer, the optical subsystem is configured as a bright field (BF) optical subsystem. Such an optical subsystem may, however, also be configured for other types of wafer inspection. For example, the optical subsystem shown in FIG. 3 may also include one or more other channels (not shown). The other channel(s) may include any of the optical components described herein such as a lens and a detector, configured as a scattered light channel. The lens and the detector may be further configured as described herein. In this manner, the optical subsystem may also be configured for dark field (DF) inspection.

Computer subsystem 302 is configured to acquire the images generated by the optical subsystem. For example, images generated by the detector(s) during scanning may be provided to computer subsystem 302. In particular, the computer subsystem may be coupled to each of the detectors (e.g., by one or more transmission media shown by the dashed lines in FIG. 3, which may include any suitable transmission media known in the art) such that the computer subsystem may receive the images generated by the detector(s).

The computer subsystem is configured for performing the steps of the computer-implemented method described further herein. The computer subsystem may be configured to perform any other step(s) of any method embodiment(s) described herein. The computer subsystem, the optical subsystem, and the system may be further configured as described herein.

It is noted that FIG. 3 is provided herein to generally illustrate one configuration of an optical subsystem that may be included in the system embodiments described herein. Obviously, the optical subsystem configuration described herein may be altered to optimize the performance of the optical subsystem as is normally performed when designing a commercial inspection system. In addition, the systems described herein may be implemented using an existing inspection system (e.g., by adding functionality described herein to an existing inspection system) such as the 29xx/28xx series of tools that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Further modifications and alternative embodiments of various aspects of the invention will be apparent to those skilled in the art in view of this description. For example, methods and systems for filtering scratches from inspection results for a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for filtering scratches from inspection results for a wafer, comprising:
generating a defect candidate map for a wafer from images of the wafer generated by a wafer inspection system, wherein the defect candidate map comprises image data for potential defect candidates as a function of position on the wafer, and wherein generating the defect candidate map comprises applying a threshold to the images and determining that portions of the images having values above the threshold are the potential defect candidates;
removing noise from the defect candidate map to generate a filtered defect candidate map;
determining one or more characteristics of the potential defect candidates based on portions of the filtered defect candidate map corresponding to the potential defect candidates;
determining if each of the potential defect candidates are scratches based on the one or more characteristics determined for each of the potential defect candidates; and
separating the potential defect candidates determined to be the scratches from other defects in inspection results for the wafer generated by the wafer inspection system, wherein the generating, removing, determining the one or more characteristics, determining if each of the potential defect candidates are the scratches, and separating steps are performed by a computer system.

2. The method of claim 1, wherein the threshold is substantially close to a noise floor of the images.

3. The method of claim 1, Wherein the images of the wafer comprise gray scale images.

4. The method of claim 1, wherein the noise that is removed from the defect candidate map comprises local color noise.

5. The method of claim 4, wherein removing the noise comprises applying a local difference filter to the images.

6. The method of claim 1, wherein the noise that is removed from the defect candidate map comprises pattern noise.

7. The method of claim 6, wherein removing the noise comprises removing horizontal and vertical pattern noise from the images.

8. The method of claim 1, wherein the one or more characteristics comprise angle of orientation of the potential defect candidates on the wafer.

9. The method of claim 1, wherein determining the one or more characteristics comprises applying a simplified Hough transform to the portions of the filtered defect candidate map corresponding to the potential defect candidates to thereby determine the one or more characteristics of the potential defect candidates.

10. The method of claim 9, wherein applying the simplified Hough transform comprises applying the simplified Hough transform to only the portions of the filtered defect candidate map corresponding to the potential defect candidates.

11. The method of claim 1, wherein the scratches comprise heads that appear stronger in the images than tails of the scratches.

12. The method of claim 11, wherein generating the inspection results for the wafer comprises applying a threshold to the images of the wafer generated by the wafer inspection system, and wherein the tails of the scratches have values in the images that are approximately equal to or less than the threshold.

13. The method of claim 11, wherein the one or more characteristics comprise magnitude of the heads and tails in the images.

14. The method of claim 11, wherein the one or more characteristics comprise angles of orientation of the heads and the tails.

15. The method of claim 11, wherein the one or more characteristics comprise number of pixels in the tails.

16. The method of claim 1, wherein the images of the wafer are generated by the wafer inspection system detecting light from the wafer.

17. The method of claim 1, wherein the scratches are caused by a chemical mechanical polishing process performed on the wafer.

18. The method of claim 1, wherein the scratches are located under a layer of the water for which the inspection results were generated.

19. The method of claim 1, wherein the scratches comprise micro-scratches.

20. A non-transitory computer-readable medium, storing program instructions executable on a computer system for performing a computer-implemented method for filtering scratches from inspection results for a wafer, wherein the computer-implemented method comprises:
generating a defect candidate map for a wafer from images of the wafer generated by a wafer inspection system, wherein the defect candidate map comprises image data for potential defect candidates as a function of position on the wafer, and wherein generating the defect candidate map comprises applying a threshold to the images and determining that portions of the images having values above the threshold are the potential defect candidates;
removing noise from the defect candidate map to generate a filtered defect candidate map;
determining one or more characteristics of the potential defect candidates based on portions of the filtered defect candidate map corresponding to the potential defect candidates;
determining if each of the potential defect candidates are scratches based on the one or more characteristics determined for each of the potential defect candidates; and
separating the potential defect candidates determined to be the scratches from other defects in inspection results for the wafer generated by the wafer inspection system.

21. A system configured to filter scratches from inspection results for a wafer, comprising:
an optical subsystem configured to direct light to a wafer and detect light from the wafer to thereby generate images for the wafer; and
a computer subsystem configured for:
generating a defect candidate map for the wafer from the images, wherein the defect candidate map comprises image data for potential defect candidates as a function of position on the wafer, and wherein generating the defect candidate map comprises applying a threshold to the images and determining that portions of the images having values above the threshold are the potential defect candidates;
removing noise from the defect candidate map to generate a filtered defect candidate map;
determining one or more characteristics of the potential defect candidates based on portions of the filtered defect candidate map corresponding to the potential defect candidates;
determining if each of the potential defect candidates are scratches based on the one or more characteristics determined for each of the potential defect candidates; and
separating the potential defect candidates determined to be the scratches from other defects in inspection results for the wafer.

22. The system of claim 21, wherein the threshold is substantially close to a noise floor of the images.

23. The system of claim 21, wherein the images of the comprise gray scale images.

24. The system of claim 21, wherein the noise that is removed from the defect candidate map comprises local color noise.

25. The system of claim 24, wherein removing the noise comprises applying a local difference filter to the images.

26. The system of claim 21, wherein the noise that is removed from the defect candidate map comprises pattern noise.

27. The system of claim 26, wherein removing the noise comprises removing horizontal and vertical pattern noise from the images.

28. The system of claim 21, wherein the one or more characteristics comprise angle of orientation of the potential defect candidates on the wafer.

29. The system of claim 21, wherein determining the one or more characteristics comprises applying a simplified Hough transform to the portions of the filtered defect candidate map corresponding to the potential defect candidates to thereby determine the one or more characteristics of the potential defect candidates.

30. The system of claim 29, wherein applying the simplified Hough transform comprises applying the simplified Hough transform to only the portions of the filtered defect candidate map corresponding to the potential defect candidates.

31. The system of claim 21, wherein the scratches comprise heads that appear stronger in the images than tails of the scratches.

32. The system of claim 31, wherein generating the inspection results for the wafer comprises applying a threshold to the images of the wafer generated by the optical subsystem, and wherein the tails of the scratches have values in the images that are approximately equal to or less than the threshold.

33. The system of claim 31, wherein the one or more characteristics comprise magnitude of the heads and tails in the images.

34. The system of claim 31, wherein the one or more characteristics comprise angles of orientation of the heads and the tails.

35. The system of claim 31, wherein the one or more characteristics comprise number of pixels in the tails.

36. The system of claim 21, wherein the scratches are caused by a chemical mechanical polishing process performed on the wafer.

37. The system of claim 21, wherein the scratches are located under a layer of the wafer for which the inspection results were generated.

38. The system of claim 21, wherein the scratches comprise micro-scratches.

* * * * *